United States Patent
Habets

(10) Patent No.: US 7,169,274 B2
(45) Date of Patent: Jan. 30, 2007

(54) MEASUREMENT DEVICE FOR DETERMINING OXYGEN ACTIVITY IN METAL OR SLAG MELTS

(75) Inventor: Danny Habets, Genk (BE)

(73) Assignee: Heraeus Electro-Nite International N.V., Houthalen (BE)

( * ) Notice: Subject to any disclaimer, the term of this patent is extended or adjusted under 35 U.S.C. 154(b) by 0 days.

(21) Appl. No.: 10/936,255

(22) Filed: Sep. 8, 2004

(65) Prior Publication Data

US 2005/0247575 A1    Nov. 10, 2005

(30) Foreign Application Priority Data

May 5, 2004    (DE)    ...................... 10 2004 022 763

(51) Int. Cl.
*G01N 27/411*    (2006.01)
(52) U.S. Cl. .................. 204/422; 204/424; 205/790
(58) Field of Classification Search ................ 204/422; 205/790
See application file for complete search history.

(56) References Cited

U.S. PATENT DOCUMENTS

| | | | |
|---|---|---|---|
| 3,578,578 A | 5/1971 | Von Krusenstierna | |
| 4,451,350 A | 5/1984 | Tsuchida et al. | |
| 4,657,641 A | 4/1987 | Nakamura et al. | |
| 5,332,449 A | 7/1994 | Verstreken et al. | |
| 5,792,329 A | 8/1998 | Curé et al. | |
| 6,855,238 B2 * | 2/2005 | Knevels et al. | ............. 204/422 |

FOREIGN PATENT DOCUMENTS

| | | |
|---|---|---|
| DE | 26 00 103 C2 | 11/1978 |
| DE | 28 10 134 A1 | 9/1979 |
| DE | 31 52 318 C2 | 11/1986 |
| DE | 41 35 510 A1 | 4/1993 |
| DE | 195 31 661 C2 | 10/1996 |
| EP | 0 295 112 A2 * | 12/1988 |
| JP | 60-052763 A | 3/1985 |
| JP | 60-085361 A | 5/1985 |

OTHER PUBLICATIONS

Iwase, M., "Rapid determination of silicon activities in hot metal by means of solid state electrochemical sensors equipped with an auxiliary electrode", *Scandinavian Journal of Metallurgy*, vol. 17, pp. 50-56 (1988).

* cited by examiner

*Primary Examiner*—Nam Nguyen
*Assistant Examiner*—Anthony Fick
(74) *Attorney, Agent, or Firm*—Akin Gump Strauss Hauer & Feld, LLP

(57) ABSTRACT

A measurement device is provided for determining the oxygen activity in molten metal or slag with a measurement head, which is arranged on one end of a carrier tube and on which an electrochemical measurement cell is arranged. The electrochemical measurement cell has a solid electrolyte tubule, which is closed on one side and which contains on its closed end a reference material and an electrode, which projects from the opposite end of the solid electrolyte tubule. The solid electrolyte tubule has on its outer surface a coating made from a mixture of zirconium silicate with a fluoride. The measurement head may also have a thermo-element, and the device may be used to determine the concentration of silicon and/or carbon in the melt, based on the oxygen activity measurement.

15 Claims, 2 Drawing Sheets

MEASUREMENT DEVICE FOR DETERMINING OXYGEN ACTIVITY IN METAL OR SLAG MELTS

BACKGROUND OF THE INVENTION

The invention relates to a measurement device for determining the oxygen activity in molten metal or slag melts with a measurement head, which is arranged at one end of a carrier tube and on which an electro-chemical measurement cell is arranged. The electrochemical measurement cell has a solid electrolyte tubule, which is closed on one side and contains on its closed end a reference material and an electrode. The electrode extends out of the opposite end of the solid electrolyte tubule. In addition, the invention relates to a solid electrolyte tubule for an electro-chemical measurement cell.

Such measurement devices are known, for example, from German Patent DE 31 52 318C2. The sensor described there is used for measuring the concentration of oxygen in molten metal. Similar measurement devices are also known from U.S. Pat. No. 3,578,578, German published patent application DE 28 10 134 A1, or German Patent DE 26 00 103 C2. In U.S. Pat. No. 4,657,641 a sensor is disclosed, which has a coating made from zirconium silicate and zirconium dioxide.

BRIEF SUMMARY OF THE INVENTION

In addition to measuring oxygen, there is also the need to measure other materials contained in the molten metal. Therefore, the invention is based on the problem of providing a simple measurement device and also a corresponding solid electrolyte tubule, which can be used to determine also the concentration of other elements, in addition to the oxygen content.

The problem is solved in that the solid electrolyte tubule has on its outer surface a coating made from a mixture of zirconium silicate with a fluoride. It has been shown that this method makes possible the determination, for example, of the concentration of silicon or carbon in the molten mass. The effect is explained in that, for example, the silicon contained in the liquid metal reacts with the $SiO_2$ from the zirconium silicate. In the equilibrium reaction, oxygen is obtained as a reaction product, and the change in the oxygen activity at the surface of the solid electrolyte is measured and correlated with the silicon content.

The measurement device can be used in molten metal or slag melts, especially in molten steel or iron, for measuring the concentration of silicon or carbon. A rapid measurement process is thereby realized. It is advantageous if the measurement device has a temperature sensor, for example a thermo-element, in addition to the electrochemical measurement cell, so that the temperature of the molten metal can also be measured. Carbon can be calculated from the silicon-carbon temperature equilibrium of the liquid metal.

By the measurement device according to the invention, sample analysis in the laboratory can be avoided, so that considerable time savings in the production process and consequently better and faster actions for influencing the production process can be achieved.

Advantageous embodiments of the invention are given below. It is expedient if the fluoride is at least one from the group $CaF_2$, $NaF$, $SrF_2$, $BaF_2$, and $MgF_2$. It is advantageous if the layer thickness equals approximately 10–100 μm, especially about 10–50 μm, and advantageously about 30 μm. Here, a thicker layer is sufficient for higher application temperatures (above approximately 1500° C.), for example before a desulfurization treatment. Here, the response time is quite short. At lower application temperatures (up to approximately 1400° C.), for example after the desulfurization treatment, a thinner layer is necessary. The response time is then somewhat greater. Advantageously, about 2–10 wt % fluoride, especially about 3–4 wt % fluoride is used (relative to the weight of the coating). At high fluoride contents, the response time at lower melt temperatures is shorter, because equilibrium can be reached more quickly. The coating can be produced very uniformly by means of plasma spraying or flame spraying.

The solid electrolyte tubule is advantageously stabilized $ZrO_2$. The layer can also cover the outer surface of the solid electrolyte tubule only partially, wherein at least the surface in the region of the tubule where the reference mass is arranged should be coated.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there is shown in the drawings an embodiment which is presently preferred. It should be understood, however, that the invention is not limited to the precise arrangements and instrumentalities shown. In the drawings.

DETAILED DESCRIPTION OF THE INVENTION

Figure 1:
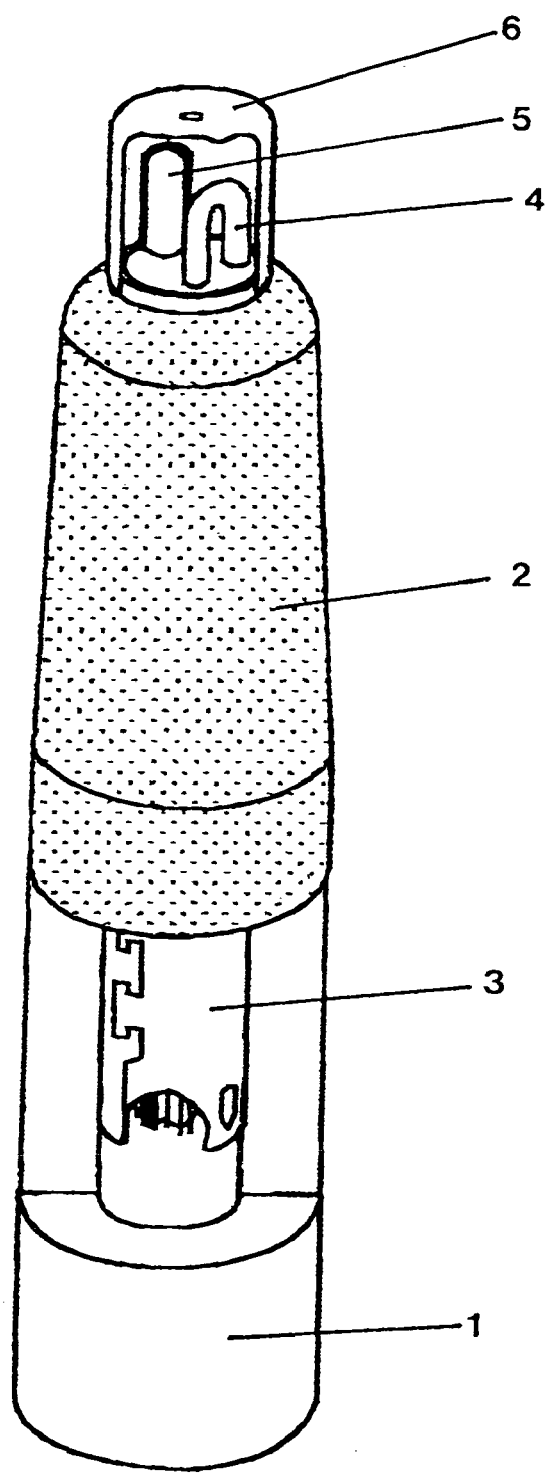
FIG. 1 is a perspective side elevation view of a measurement device according to the invention.

The measurement device has a carrier tube 1, in which the measurement head 2 is held, wherein by means of a contact piece 3 within the carrier tube 1 the measurement head 2 contacts a supply line to measurement and evaluation instruments. The carrier tube 1 is shown in FIG. 1 only at the attachment part.

At the immersion end of the measurement head, in addition to a thermo-element 4, there is a solid electrolyte tubule 5. Thermo-element 4 and solid electrolyte tubule 5 are surrounded by a protective cap 6 and protected before or during the immersion of the measurement head into the melt, especially an iron or steel melt.

Figure 2:
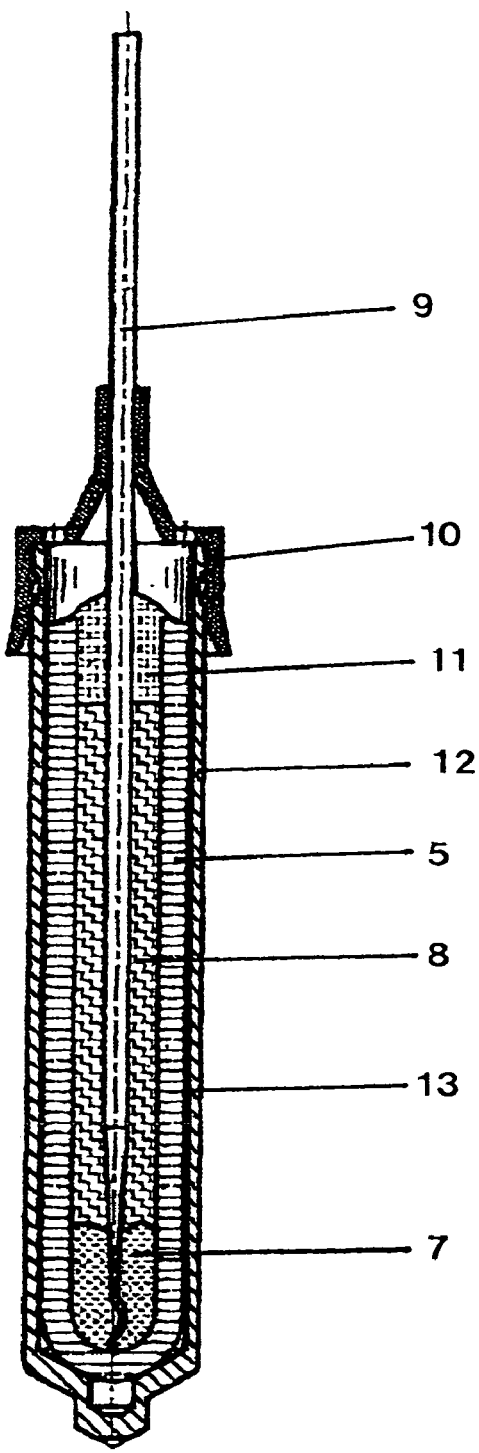
FIG. 2 is a longitudinal cross sectional view through the solid electrolyte tubule.

In FIG. 2 the solid electrolyte tubule 5 is shown in section. It is produced from stabilized zirconium dioxide and has in its interior as reference material 7 a mixture of molybdenum and molybdenum dioxide, a mixture of chromium and chromium dioxide, or a mixture of nickel and nickel oxide. The filler material 8 arranged above the reference material is, for example, aluminum oxide. In the solid electrolyte tubule 5, a molybdenum rod is arranged centrally as an electrode 9. The electrode 9 projects from the open end of the solid electrolyte tubule 5. This open end is closed by a cap 10, wherein the filler material 8 is held at its upper end by a gas-permeable cement 11. The solid electrolyte tubule 5 is surrounded by a steel cap 12, which also protects the tubule during the immersion into the melt. The steel cap 12 then melts and exposes the coating 13 arranged on the solid electrolyte tubule 5. The coating is preferably a mixture of zirconium silicate and about 3–4 wt % magnesium fluoride. The coating is approximately 30 μm and is applied by plasma-spraying.

In the melt $SiO_2$ reacts with the Si of the melt, wherein oxygen is released in an equilibrium reaction, and its activity is measured with the help of the solid electrolyte tubule.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A measurement device for determining oxygen activity in metal or slag melts, comprising a measurement head arranged on one end of a carrier tube and an electrochemical measurement cell arranged on the measurement head, the electrochemical measurement cell having a solid electrolyte tubule, the tubule having a closed end which contains a reference material and an electrode, wherein the electrode projects from an opposite end of the tubule toward the carrier tube, and wherein the solid electrolyte tubule comprises stabilized $ZrO_2$, and an outer surface of the tubule is at least partially covered with a coating comprising a mixture of zirconium silicate with a fluoride, the coating being plasma-sprayed, having a thickness of about 10–100 μm, and containing the fluoride in an amount of about 2 to 4 wt % based on the weight of the coating.

2. The measurement device according to claim 1, wherein the fluoride is at least one selected from the group consisting of $CaF_2$, $NaF$, $SrF_2$, $BaF_2$, and $MgF_2$.

3. The measurement device according to claim 1, wherein the fluoride is present in an amount of about 3 to 4 wt % based on the weight of the coating.

4. The measurement device according to claim 1, wherein the coating has a thickness of about 10–100 μm.

5. The measurement device according to claim 1, further comprising a thermo-element on the measurement head for measuring a temperature of the melt.

6. A method for determining carbon content in a metal or slag melt, comprising immersing the measurement head of the device according to claim 5 in a melt to be measured, measuring a change in oxygen activity at the outer surface of the solid electrolyte tubule, correlating the measured change in oxygen activity with silicon content, measuring the temperature of the melt, and calculating the carbon content from a silicon-carbon temperature equilibrium of the melt.

7. The method according to claim 6, wherein the melt is steel or iron.

8. A method for determining silicon content in a metal or slag melt, comprising immersing the measurement head of the device according to claim 1 in a melt to be measured, measuring a change in oxygen activity at the outer surface of the solid electrolyte tubule, and correlating the measured change in oxygen activity with silicon content.

9. The method according to claim 8, wherein the melt is steel or iron.

10. The measurement device according to claim 1, wherein at least the surface of the tubule in a region where the reference material is arranged is covered by the coating.

11. A solid electrolyte tubule for an electrochemical measurement cell, the tubule having a closed end and comprising stabilized $ZrO_2$, and an outer surface of the tubule being at least partially covered with a coating comprising a mixture of zirconium silicate with a fluoride, the coating being plasma-sprayed, having a thickness of about 10–100 μm, and containing the fluoride in an amount of about 2 to 4 wt % based on the weight of the coating.

12. The solid electrolyte tubule according to claim 11, wherein the fluoride is at least one selected from the group consisting of $CaF_2$, $NaF$, $SrF_2$, $BaF_2$, and $MgF_2$.

13. The solid electrolyte tubule according to claim 11, wherein the fluoride is present in an amount of about 3 to 4 wt % based on the weight of the coating.

14. The solid electrolyte tubule according to claim 11, wherein the coating has a thickness of about 10–50 μm.

15. The solid electrolyte tubule according to claim 11, wherein at least the surface of the tubule in a region where the reference material is arranged is covered by the coating.

* * * * *